(12) United States Patent
Kofler

(10) Patent No.: US 10,850,284 B2
(45) Date of Patent: Dec. 1, 2020

(54) PIPETTE-TIP-ACCOMMODATING CONTAINER AND METHOD FOR PROVIDING THE SAME

(71) Applicant: Greiner Bio-One GmbH, Kremsmuenster (AT)

(72) Inventor: Georg Kofler, Inzersdorf im Kremstal (AT)

(73) Assignee: Greiner Bio-One GmbH, Kremsmuenster (AT)

(*) Notice: Subject to any disclaimer, the term of this patent is extended or adjusted under 35 U.S.C. 154(b) by 329 days.

(21) Appl. No.: 15/753,814

(22) PCT Filed: Aug. 18, 2016

(86) PCT No.: PCT/AT2016/060031
§ 371 (c)(1),
(2) Date: Feb. 20, 2018

(87) PCT Pub. No.: WO2017/031514
PCT Pub. Date: Mar. 2, 2017

(65) Prior Publication Data
US 2019/0009277 A1    Jan. 10, 2019

(30) Foreign Application Priority Data

Aug. 21, 2015 (AT) .............................. A 50732/2015

(51) Int. Cl.
*B65D 1/00* (2006.01)
*B01L 3/02* (2006.01)
*B01L 9/00* (2006.01)

(52) U.S. Cl.
CPC ......... *B01L 9/543* (2013.01); *B01L 2200/025* (2013.01); *B01L 2200/028* (2013.01);
(Continued)

(58) Field of Classification Search
None
See application file for complete search history.

(56) References Cited

U.S. PATENT DOCUMENTS 5,344,023 A * 9/1994 Cox .................. A47J 47/02
206/508
6,019,225 A * 2/2000 Kalmakis ............ B01L 9/543
206/563
(Continued)

FOREIGN PATENT DOCUMENTS

CN 1642651 A 7/2005
CN 1948967 A 4/2007
(Continued)

OTHER PUBLICATIONS

International Search Report of PCT/AT2016/060031, dated Dec. 7, 2016.
(Continued)

*Primary Examiner* — Marc C Howell
*Assistant Examiner* — Brittany I Fisher
(74) *Attorney, Agent, or Firm* — Collard & Roe, P.C.

(57) ABSTRACT

The invention relates to a pipette-tip-accommodating container (1), including a receiving cradle (3) and a cover (4) which covers a receiving opening (12) of the receiving cradle (3) in its closed position. The cover (4) comprises a standardized footprint and is realized as an adapter element for the receiving cradle (3). A positioning device (25) with multiple positioning elements (26) is provided on the cover (4). The receiving cradle (3) is supported on the cover (4) by way of its base (7), wherein the receiving cradle (3) is aligned relatively with reference to the footprint defined by the cover (4), positioned in a positioning position for automated sample processing by means of the positioning elements (26). Furthermore, the invention also relates to a
(Continued)

method for providing such a pipette-tip-accommodating container (1).

17 Claims, 8 Drawing Sheets

(52) U.S. Cl.
CPC . *B01L 2300/043* (2013.01); *B01L 2300/0851* (2013.01); *B01L 2300/0858* (2013.01)

(56) References Cited

U.S. PATENT DOCUMENTS

| | | | |
|---|---|---|---|
| 6,221,317 B1 | 4/2001 | Carl | |
| 6,534,015 B1* | 3/2003 | Viot | B01L 9/543 |
| | | | 422/564 |
| 7,168,286 B1 | 1/2007 | Pelech | |
| 7,906,075 B2 | 3/2011 | Ueda | |
| 9,433,944 B2 | 9/2016 | Blumentritt et al. | |
| 10,267,815 B2 | 4/2019 | Knofe et al. | |
| 2002/0009398 A1* | 1/2002 | Labriola | B01L 9/543 |
| | | | 422/564 |
| 2005/0133512 A1* | 6/2005 | Prokopp | B01L 9/543 |
| | | | 220/601 |
| 2005/0133515 A1 | 6/2005 | Gutierrez et al. | |
| 2005/0150808 A1* | 7/2005 | Sarna | B01L 9/543 |
| | | | 206/562 |
| 2006/0093530 A1* | 5/2006 | Ueda | B01L 9/543 |
| | | | 422/400 |
| 2008/0240999 A1 | 10/2008 | Timpson et al. | |
| 2009/0139296 A1 | 6/2009 | McCauley | |
| 2010/0307956 A1 | 12/2010 | Lepot | |
| 2012/0328489 A1* | 12/2012 | Beese | B01L 9/543 |
| | | | 422/526 |
| 2013/0336852 A1* | 12/2013 | Rethwisch | B01L 9/543 |
| | | | 422/564 |
| 2014/0234182 A1* | 8/2014 | Motadel | B01L 9/543 |
| | | | 422/526 |
| 2014/0271412 A1* | 9/2014 | Hovatter | B65D 43/22 |
| | | | 422/564 |
| 2016/0001292 A1 | 1/2016 | Motadel et al. | |

FOREIGN PATENT DOCUMENTS

| | | |
|---|---|---|
| CN | 101752281 A | 6/2010 |
| CN | 102962111 A | 3/2013 |
| CN | 203427005 U | 2/2014 |
| CN | 104150101 A | 11/2014 |
| DE | 103 61 167 A1 | 7/2005 |
| EP | 2 535 109 A2 | 12/2012 |
| EP | 2 789 389 A1 | 10/2014 |
| GB | 1 527 212 A | 10/1978 |
| JP | H08-233829 A | 9/1996 |
| JP | 2015-508888 A | 3/2015 |
| WO | 2009/053434 A1 | 4/2009 |
| WO | 2014/130679 A1 | 8/2014 |

OTHER PUBLICATIONS

Letter of Austrian Patent Attorney to European Patent Office in PCT/AT2016/060031, dated Jun. 20, 2017 with English translation of relevant parts.
Japanese Office Action in Japanese Patent Application 2018-528365 dated Aug. 4, 2020 with English translation.
Search Report in in Japanese Patent Application No. 2018-528365 dated Jul. 29, 2020 with English translation.

* cited by examiner

PIPETTE-TIP-ACCOMMODATING CONTAINER AND METHOD FOR PROVIDING THE SAME

CROSS REFERENCE TO RELATED APPLICATIONS

This application is the National Stage of PCT/AT2016/060031 filed on Aug. 18, 2016, which claims priority under 35 U.S.C. § 119 of Austrian Application No. A 50732/2015 filed on Aug. 21, 2015, the disclosure of which is incorporated by reference. The international application under PCT article 21(2) was not published in English.

BACKGROUND OF THE INVENTION

1. Field of the Invention

The invention relates to a pipette-tip-accommodating container for receiving a plurality of pipette tips according to one aspect of the invention. However, the invention also relates to a method for providing a pipette-tip-accommodating container for receiving a plurality of pipette tips according to another aspect of the invention.

2. Description of the Related Art

U.S. Pat. No. 6,221,317 B1 has disclosed a generic device for providing pipette tips where the basic body comprises the standardized standing area with the determined length dimension and with the determined width dimension which is aligned at right angles thereto. To obtain the standardized standing area, the basic body is realized in its outer peripheral region with a predominantly double-walled wall structure, the outer doubled wall parts forming the standardized standing area here. Webs, which extend up to its open top side and intersect one another, are arranged in the interior of the basic body, thereby forming indentations arranged in a predetermined grid between them. A carrier plate with openings which are arranged therein and serve for receiving the pipette tips is supported on said webs. The number and the grid arrangement of the openings in the carrier plate is chosen in dependence on the size and the number of the pipette tips to be received on the carrier plate and on the determined standard (SBS-standard). The grid arrangement of the webs in the base body enables the use of carrier plates which vary with respect to one another with reference to the number of pipette tips to be received and to the arrangement thereof on the carrier plate. In this way, the identical basic body with the standardized standing area can always be used for providing the pipette tips. To this end, only the carrier plate that corresponds to the respective application must be used in order to obtain, by means of the basic body, the positioning of the pipette tips necessary for automated sample processing. The basic body of the providing device is also closable on its top side with a fittable cover. With the cover fitted on the basic body in each case, multiple similarly realized providing devices can also be arranged one above another to form a stack. To this end, interacting positive locking structures are provided on the top side of the cover and on the bottom side of the base body.

US 2014/0234182 A1 and the resulting WO 2014/130679 A1 describe a pipette-tip-accommodating container for receiving a plurality of pipette tips. The pipette-tip-accommodating container includes a receiving cradle with a base and with side walls which project up from the base. The side walls surround a receiving opening at least in portions and together with the base define a receiving area. Furthermore, the pipette-tip-accommodating container includes a cover with a cover wall and with cover side walls which stand out from the cover wall, the cover side walls together with the cover wall defining a cover interior. A carrier with receiving openings arranged therein for the aligned receiving of the pipette tips is arranged in the receiving cradle in the region of its receiving opening. Furthermore, the receiving cradle is realized in a single-walled manner in the region of its side walls. With the cover in the closed position, it covers the receiving opening of the receiving cradle, the cover being held on the receiving cradle so as to be removable. The receiving cradle, on its outside and in the region of its base, comprises support elements which jut out in the direction turned away from the receiving area. The support elements serve for forming a standardized standing area (footprint) for the receiving cradle. In addition, ribs, which jut out in the direction turned away from receiving area and are connected to the side wall and the support element, can be arranged in the region of the side walls and of the support elements. A disadvantage in this case is that as a result of the additional support elements, a higher material requirement per receiving cradle is necessary for production and, over and above this, the receiving cradle is also more difficult to grasp for manual handling.

SUMMARY OF THE INVENTION

The object underlying the present invention is to overcome the disadvantages of the prior art and to make available a universally usable pipette-tip-accommodating container which can be produced in a simple and cost-efficient manner with a low raw material requirement and which can be used both for manual sample processing and automatic sample processing. Over and above this, however, it should also be possible to transport and store structurally identical receiving cradles in a space-saving manner through to the completion thereof.

Said object of the invention is achieved as a result of
  the cover, in its outer peripheral region at least in portions, defining a standing area (footprint) which is standardized according to standard SLAS 1-2004 (R2012) of the American National Standards Institute (ANSI) with a length dimension with a value of 127.76 mm±0.25 mm and with a width dimension, which is aligned at right angles thereto, with a value of 85.48 mm±0.25 mm,
  a positioning device with multiple positioning elements which are arranged distributed, in particular over the periphery of the cover, being provided on the cover,
  the cover, in an open position removed from the receiving cradle, forming an adapter element for the receiving cradle, and
  the receiving cradle, with the cover in the removed open position, being supported by way of its base on the cover, which has been removed from the receiving cradle, for forming an adapter position, and in said adapter position, the receiving cradle is aligned relatively with reference to the standing area (footprint) defined by the cover positioned in a positioning position for automated sample processing by means of the positioning elements.

The advantage achieved as a result is that, in this way, the receiving cradle can be produced in a simple, material-saving realization which is also easy to grasp for manual handling. In this case, the cover of the pipette-tip-accommodating container serves as an adapter element for the support and precise positioning of the receiving cradle for automated sample processing and the receiving cradle is able to be realized in its dimensions, in particular in the region of its base, independently of the standardized dimensions for automated sample processing and can nevertheless be used for both types of sample processing. As a result, when realizing the receiving cradle, a not inconsiderable quantity or amount of material, in particular plastics material, is able to be saved. Furthermore, the receiving cradle is also able to be produced with simple molding tools. By using less material, however, production can also be effected with shorter cycle times, as a result of which savings are also achievable. Over and above this, in this way, the shape of the outline of the cover can be adapted in a simple manner to the standardized dimensions of the standing area. Consequently, in their outer peripheral region, the cover side walls can be realized in an almost linear and planar manner in the region of the cover wall. It is consequently possible to dispense with additional stop means or the like in order to retain and realize the standardized dimensions as positioning stops.

Furthermore, the cover is consequently matched and realized precisely to the dimensions stipulated according to the standard. As a result of determining and maintaining the standardized dimensions, only the outer dimensions of the cover are to be matched thereto and the receiving cradle can be realized in a simpler and more material-saving manner. In a preferred manner, the cover side walls can consequently be realized in a linear or planar manner without additional projections or the like for the precise maintaining of the standardized standing area.

A further realization provides that the positioning device is arranged or realized in the cover interior of the cover and in the region of its cover wall. Consequently, the cover interior of the cover is able to serve for receiving and supporting the receiving cradle. Furthermore, a smaller space requirement is consequently also able to be obtained in the adapter position as the cover side walls project up from the cover wall at the side of the receiving cradle.

Furthermore, it can be advantageous when the positioning device is arranged or realized on the cover wall and on its side turned away from the cover interior. Consequently, the cover can fulfill a dual function. On the one hand, it can realize the adapter element for the receiving cradle and, on the other hand, at the same time it can also form the positioning elements for forming a stack of multiple pipette-tip-accommodating containers.

Another embodiment is characterized in that the receiving cradle is supported directly on the cover wall in the positioning position thereof. As a result, the receiving cradle is able to be fed to the automated sample processing or for the removal of pipette tips with only a small additional protrusion with reference to its own installation height. Furthermore, however, it can also improve the strength of the receiving cradle in the cover and avoid unintentional tilting.

A further possible embodiment has the feature that the receiving cradle is supported in each case in the transition regions between the side walls, which are arranged one behind another in the peripheral direction, against said side walls and in the peripheral region thereof, which faces the base, against said positioning elements. Consequently, the individual positioning elements can be realized in the region of the cover interior with a relatively small protrusion above the cover wall and nevertheless sufficient and secure relative positioning with respect to one another can be achieved.

A further embodiment provides that two positioning elements are provided on the cover, in particular on the cover wall thereof, for each of the transition regions of the receiving cradle. Consequently, the receiving cradle can be positioned precisely in the cover in each of its corner or transition regions between the individual side walls. As a result of said plurality of positioning elements, the receiving cradle can thus be better guided as early as during the insertion operation into the cover interior and can then be aligned in a precisely positioned manner and can be held in said position so as to be almost non-displaceable.

A further preferred embodiment is characterized in that, with the receiving cradle situated in the positioning position, it is aligned centrally with reference to the standing area (footprint) defined by the cover. Consequently, the receiving cradle can be inserted into the cover interior simply and independently of the relative position of the cover without prior mutual alignment.

Furthermore, it can be advantageous when the cover is pivotably mounted on the receiving cradle by means of at least one pivoting arrangement. As a result, the cover is able to be pivoted up simply for manual sample processing in order, thus, to enable access to the pipette tips stored or received in the pipette-tip-accommodating container. Furthermore, however, this also forms an associated structural unit made up of receiving cradle and cover.

Another alternative embodiment is characterized in that the receiving cradle is realized in a single-walled manner in the region of its side walls. As a result of the single-walled receiving cradle, realized at least in the region of the side walls, a large saving in material can thus be obtained. Over and above this, however, simpler realized tools can thus also be used for forming the receiving cradle.

A further possible and, where applicable, alternative embodiment has the feature that the side walls of the receiving cradle are realized tapering conically, when seen in axial section, in each case proceeding from the receiving opening in the direction of the base, and that the receiving cradle comprises a clear cross sectional dimension in the region of its receiving opening which is realized greater than an outer cross sectional dimension of the receiving cradle in the region of the base. Consequently, the basic option can be created of being able to stack identically constructed receiving cradles in one another in a space-saving manner up until the joining or fitting of the cover. By choosing the corresponding opening width of the receiving opening, it is thus possible to determine the size of the stack height of receiving cradles stacked in one another in the same way that is achievable. The greater the difference in the cross sectional dimensions, the deeper and all the more space-saving is the manner in which multiple receiving cradles are able to be stacked into one another and there is thus a smaller volume for transport and storage.

Another embodiment is characterized in that at least one first stacking means is arranged or realized on the receiving cradle in the region of its receiving area, and a further structurally identical receiving cradle is insertable into the receiving area and is supportable on the at least one stacking means. As a result of the mutual stop limitation, reciprocal jamming of receiving cradles when forming the stack thereof can be prevented.

A further preferred embodiment is characterized in that the base of the receiving cradle at least in regions forms a further stacking means. As a result, with the smallest amount of expenditure it is possible to stack multiple structurally identical receiving cradles into one another.

A further embodiment provides that a carrier with centering receiving means arranged therein for the aligned receiving of the pipette tips is arranged or realized in the receiving cradle in the region of its receiving opening. This creates the possibility of being able to provide the pipette tips in a corresponding precise alignment inside the pipette-tip-accommodating container.

Another embodiment is characterized in that, in its closed position, the cover is held in a locked manner on the receiving cradle by means of at least one closing device, wherein the at least one closing device includes a first closing element on the cover and a second closure element which interacts therewith on the receiving cradle. Unintentional opening of the cover can be prevented as a result of the closure elements engaging one another. Protected storage of the pipette tips can consequently be achieved.

A further preferred embodiment is characterized in that the first closure element, which is arranged on the cover, in particular on at least one of its cover side walls, is realized in a lobe-shaped manner and is connected to the cover so as to be pivotable, and in that, with the receiving cradle situated in the positioning position, the first closure element is pivoted into the cover interior and abuts against the side wall of the receiving cradle which is arranged directly adjacent. As a result of the lobe-shaped realization of the closure element, it can be used in multiple functions. In the normal position of use, the first closure element serves for the purpose of holding the cover on the receiving cradle locked in its closed position. In a further use, the further closure element also serves for the purpose of being pivoted into the space realized between the side walls of the receiving cradle and the cover side walls. As a result of said pivoting and projecting into the space, a pressure force can thus be exerted onto the receiving cradle on account of the restoring action of the lobe-shaped closure element. Furthermore, parts on the cover which stick out to the side beyond the outer extent of the cover and could be troublesome or even obstructive during automated sample processing, can consequently be avoided.

Another embodiment is characterized in that, with the receiving cradle in the positioning position, side walls of the receiving cradle and cover side walls of the cover, which are arranged directly adjacent one another, are aligned in each case extending substantially parallel to one another, when seen in the peripheral direction. As a result, a simple optical check can be provided by the user in order, in this way, to be able to check in a simple manner the precise positioning of the receiving cradle in the cover.

The object of the invention, however, independently thereof, can also be achieved by a method for providing a pipette-tip-accommodating container for receiving a plurality of pipette tips according to the features according to another aspect of the invention. The advantages obtained from the combination of features of said claim consist in that, as a result, the receiving cradle is able to be produced in a simple, material-saving realization which is also easy to grasp for manual handling. In this case, the cover of the pipette-tip-accommodating container serves as an adapter element for the receiving and precise positioning of the receiving cradle for automated sample processing and the receiving cradle is able to be realized in its dimensions, in particular in the region of its base, independently of the dimensions standardized for automated sample processing and nevertheless is able to be used for both types of sample processing. As a result, when realizing the receiving cradle, a not inconsiderable quantity or amount of material, in particular plastics material, is able to be saved. Furthermore, the receiving cradle is also able to be produced with simple molding tools. By using less material, however, production can also be effected with shorter cycle times, as a result of which savings are also achievable.

A further advantageous method of operation is characterized in that the receiving cradle, in the positioning position thereof in the cover, is aligned centrally with reference to the standing area (footprint) defined by the cover. The receiving cradle can consequently be inserted simply and independently of the relative position of the cover into the cover interior without prior reciprocal alignment.

Finally, a method variant is also advantageous where the receiving cradle, in the positioning position thereof in the cover, is acted upon additionally with an actuating force, which is aligned approximately parallel with reference to the cover wall, acting on at least one of its side walls, and the receiving cradle is pressed in the effective direction of the actuating force by said force against at least individual positioning elements of the positioning elements. Consequently, a targeted pressing force onto the receiving cradle and furthermore onto the oppositely situated positioning elements can be exerted by the first closure element in the position thereof pivoted into the space realized between the side walls of the receiving cradle and the cover side walls.

BRIEF DESCRIPTION OF THE DRAWINGS

For better understanding of the invention, it will now be explained in more detail by way of the following figures.

Each figure is a strongly simplified schematic representation as follows.

DETAILED DESCRIPTION OF THE PREFERRED EMBODIMENTS

Figure 1:
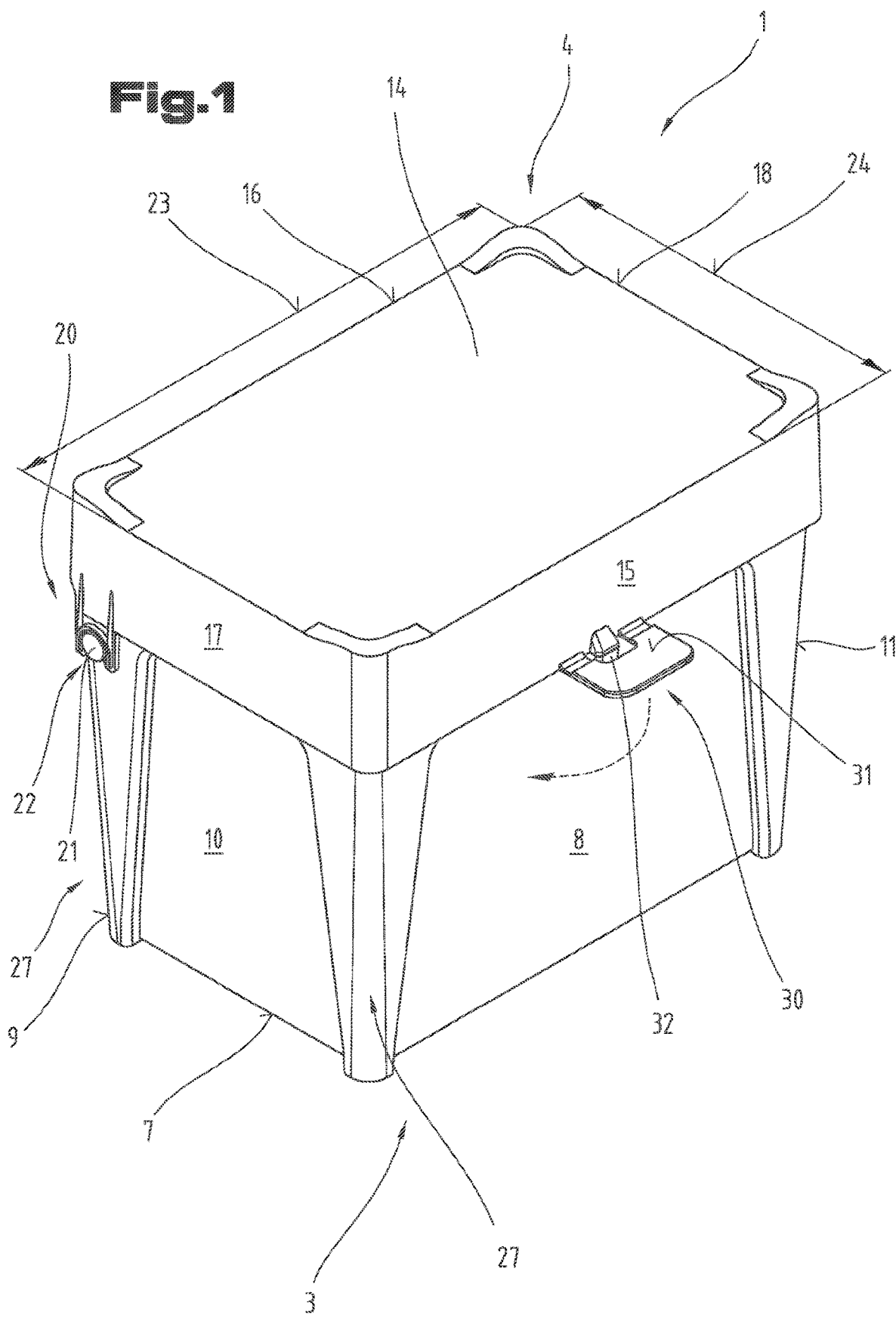
FIG. 1 shows a diagrammatic representation of a pipette-tip-accommodating container with the cover in the closed position on the receiving cradle.

It is to be noted as an introduction that identical parts are provided with identical reference signs or identical component designations in the variously described embodiments, the disclosures included in the entire description being able to be transferred analogously to identical parts with identical reference signs or identical component designations. The positional specifications chosen in the description, such as, for example, up, down, to the side etc. are also with reference to the figure directly described and shown and said positional specifications are to be transferred to the new position in an analogous manner when there is a change in position.

The term "in particular" is to be understood below such that, in this case, it can be a possible more special realization or more detailed specification of an object or of a method step, but does not necessarily have to provide a mandatory preferred embodiment of the same or a method of operation.

FIGS. 1 to 7 show a pipette-tip-accommodating container 1 for receiving a plurality of pipette tips 2 which includes a receiving cradle 3, a cover 4 and a carrier 5 with centering receiving means 6 for the pipette tips 2 arranged or realized therein. The arrangement with respect to one another of the plurality of centering receiving means 6 is standardized for the most part. In a preferred manner, the longitudinal and transverse distances between the center lines of the centering receiving means 6 are in each case 9.00 mm, said longitudinal and transverse distances also having to be chosen in accordance with the corresponding standard. The centering receiving means 6 serve for receiving the pipette tips 2 in an aligned manner, as is adequately known in the case of such pipette-tip-accommodating containers 1.

The receiving cradle 3, in turn, includes a base 7 and side walls 8 to 11 which are each aligned projecting up from the base. The side walls 8 to 11 surround at least in regions, at their ends distanced from the base 7, a receiving opening 12 and together with the base 7 define a receiving area 13.

The cover 4, in the case of said exemplary embodiment, includes a cover wall 14 and, in the peripheral region of the same, cover side walls 15 to 18 which stand out from said cover. The cover side walls 15 to 18, together with the cover wall 14, define a cover interior 19. On the top side or outside of the cover 4, on the outer periphery thereof, positioning aids are arranged in each case in the corner regions, which positioning aids serve for the purpose of holding the base of a preferred structurally identical receiving cradle 3 against slipping so as to form a stack of multiple closed pipette-tip-accommodating containers 1 one above another. The positioning aids are not provided extending over the entire periphery of the cover 4 here but only in the corner regions.

Figure 2:
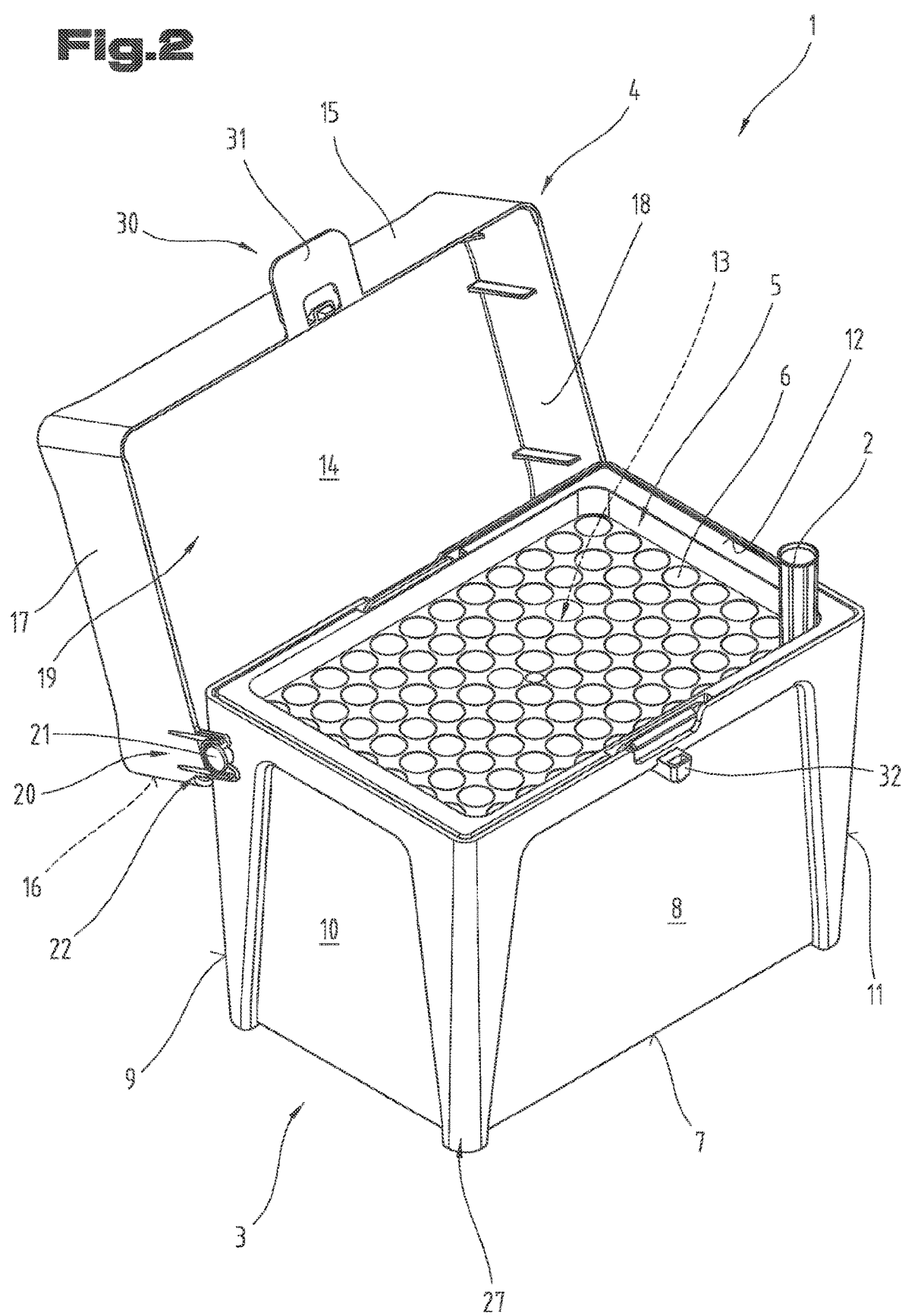
FIG. 2 shows a diagrammatic representation of the pipette-tip-accommodating container according to FIG. 1, but with the cover in the open position.
Figure 3:
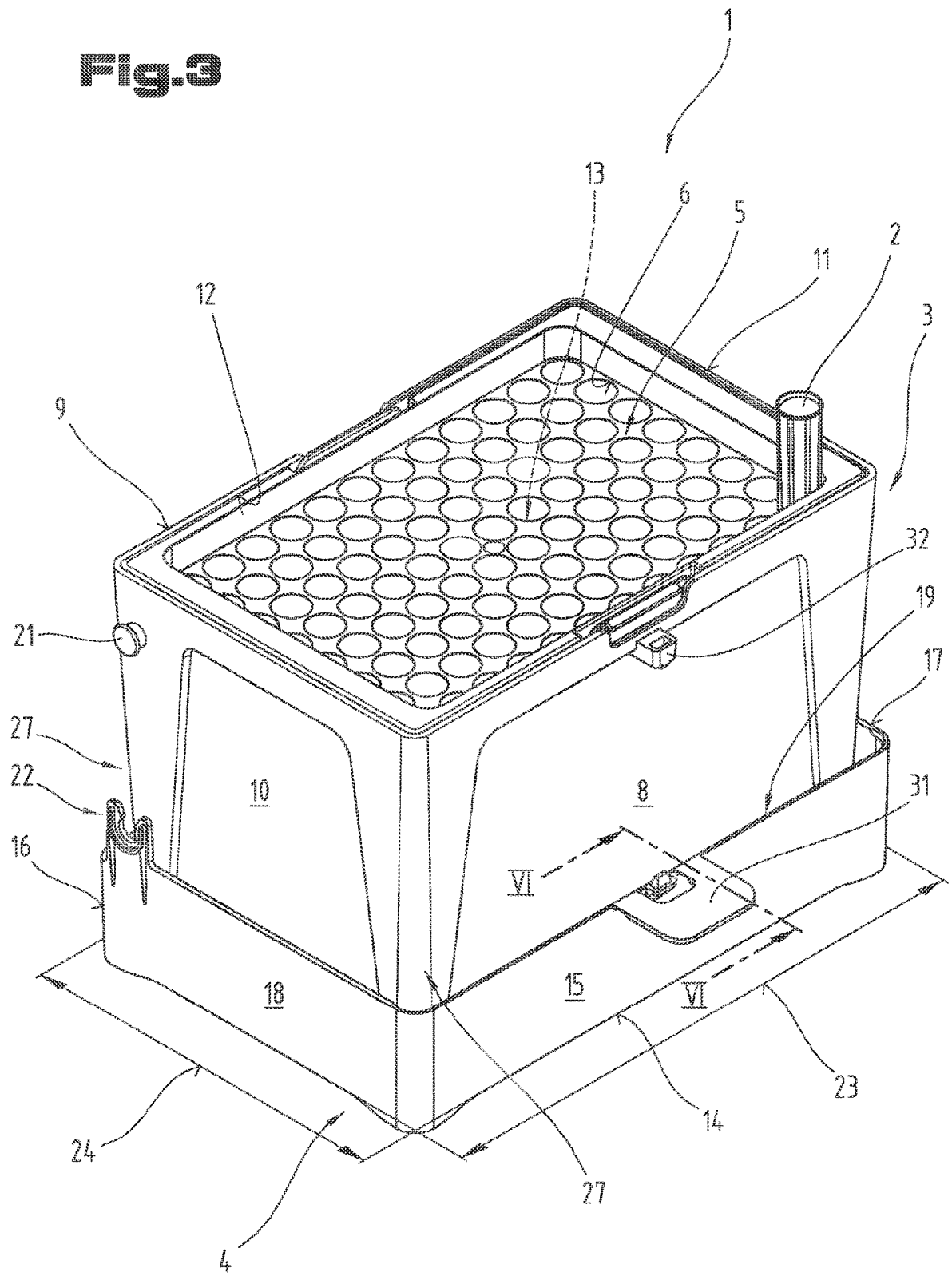
FIG. 3 shows a diagrammatic representation of the pipette-tip-accommodating container according to FIGS. 1 and 2, but with the cover removed from the receiving cradle and with the receiving cradle in the positioning position inserted in the cover.

In the closed position shown in FIG. 1, the cover 4 covers the receiving opening 12 of the receiving cradle 3. Furthermore, the cover 4 is held on the receiving cradle 3 so as to be removable. This can be effected either by a pure push-on connection, the cover side walls 15 to 18 being able to overlap the side walls 8 to 11 of the receiving cradle 3 on the outside at least in regions. In the case of said exemplary embodiment, it is shown that the cover 4 is pivotably mounted on the receiving cradle 3 by means of at least one pivoting arrangement 20. To this end, pivot pins 21 are arranged in the region of each of the two narrower or shorter side walls 10, 11, in particular are integrally formed in one piece thereon. A pivot eyelet 22, which can best be seen from an overview in FIGS. 1 to 3, is arranged on the cover 4, in particular on the cover side walls 17 and 18 which are also realized here in each case in a shorter manner. The pivot eyelet or eyelets 22 are realized in such a manner that, on the one hand, the cover 4 is able to pivot about the pivot pin or pivot pins 21 and the cover 4 is removable from the pivot pin or the pivot pins 21 as a result of elastic deformation of the eyelet or of the eyelets 22. The removal and the further use of the cover 4 will be described in more detail below.

Figure 4:
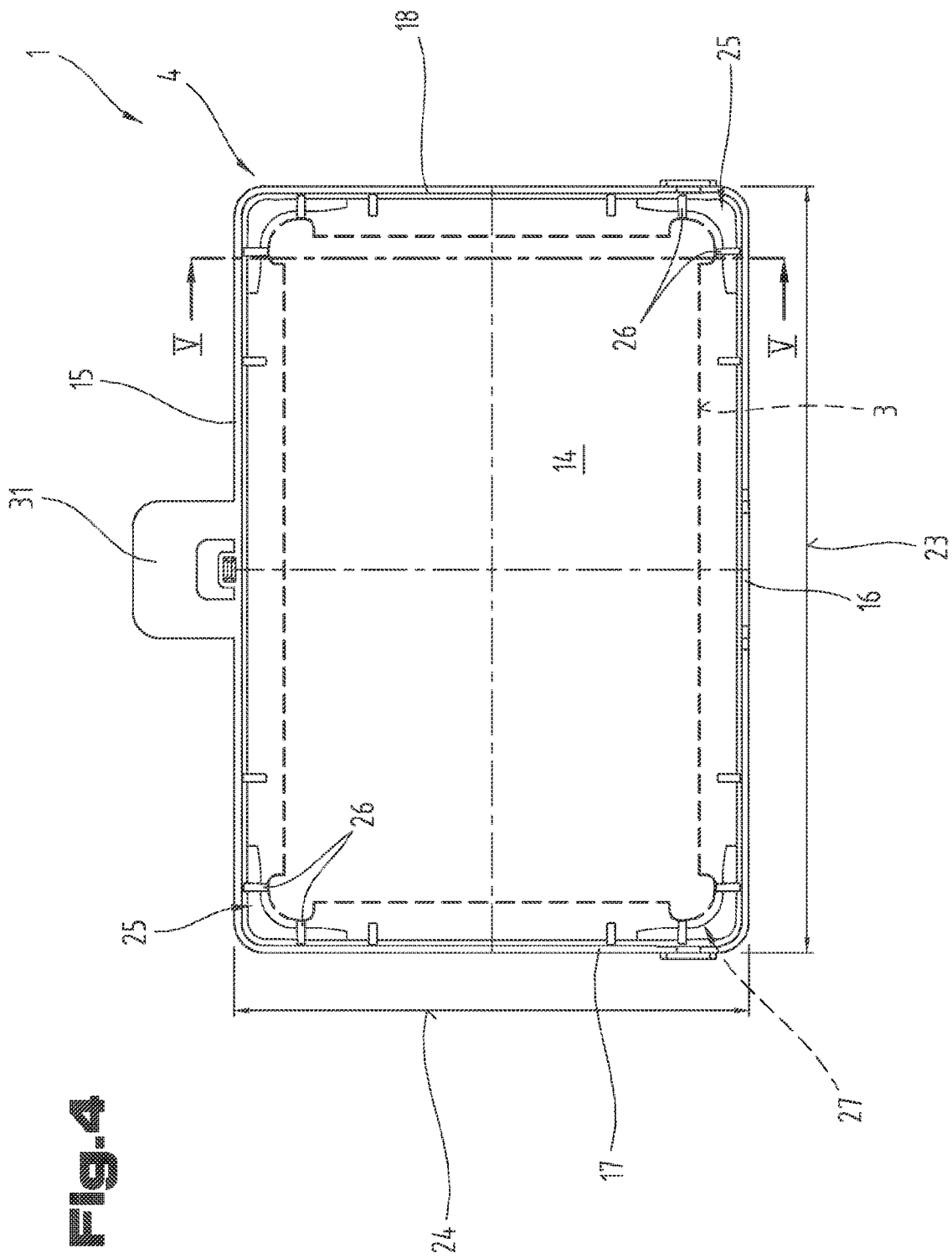
FIG. 4 shows the cover of the pipette-tip-accommodating container in a view of its cover interior, with the outline of the receiving cradle indicated.
Figure 5:
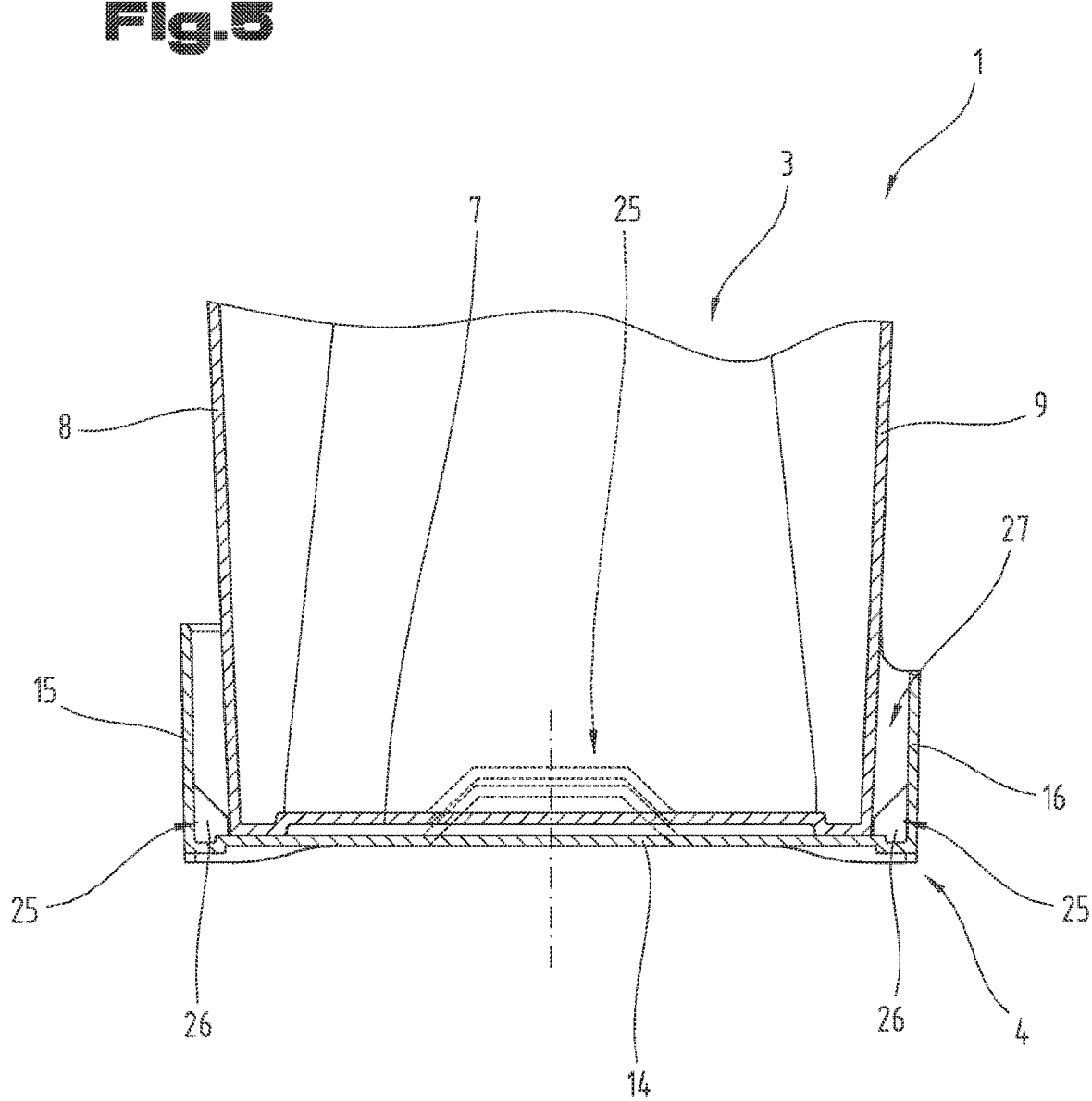
FIG. 5 shows a side view sectioned according to the lines V-V in FIG. 4 of a part detail of the cover and of the receiving cradle accommodated therein in the region of the positioning device.

As can now be seen better from the representations in FIGS. 3 to 5, the cover 4 is realized as an adapter element for the receiving cradle 3. An adapter element is to be understood here as the cover 4 defining in its outer peripheral region, at least in portions, a standardized standing area with a length dimension 23 and a width dimension 24 which is aligned at a right angle thereto. The standardized standing area can also be designated as a so-called "footprint". In the most varied laboratories, standardized dimensions of the footprint have been introduced for automated sample processing in order, in this way, to be able to accommodate and process the variously designed pipette-tip-accommodating containers 1, as are commercially available from different manufacturers, using automated systems. Automated sample processing is to be understood here in general as pipette tips 2 being moved into a precisely determined position in the system and remaining in said system in the positioned location or position for the automatic removal of individual or multiple pipette tips 2. As the pipette tips 2 are received in the receiving cradle 3 itself in a predetermined grid pattern, the receiving cradle 3 must be moved into the precisely determined position. In the case of said realization, the cover 4 then serves for the purpose of, on the one hand, forming the footprint which is standardized for the positioning and, on the other hand, being able to receive the receiving cradle 3 positioned in such a manner that the pipette tips 2 are arranged with respect thereto with reference to the standardized footprint.

In order to be able to ensure a reciprocal positioned alignment of the receiving cradle 3 in the cover 4, a positioning device 25 is provided in the region of the cover wall 14 of the cover 4. The positioning device 25, in turn, can include multiple positioning elements 26 which are distributed, in particular, over the periphery of the cover 4. In the case of the exemplary embodiment shown here, the positioning elements 26 are allocated to the outer peripheral edge of the base 7 or of the side walls 8 to 11 or interact with the same.

However, it would also be possible, independently of this, to provide multiple positioning elements 26 on the cover wall 14 on its side facing the base 7 in the positioning position, which positioning elements project beyond the cover wall 14 and each engage in a centering opening arranged or realized in the base 7 in the positioning position. Said realization is indicated in dashed lines in a simplified manner in the base region of FIG. 5.

If the cover 4 is used as an adapter element for the receiving cradle 3, the cover 4 is to be moved from the receiving cradle 3 into an open position. It consequently becomes possible to place the receiving cradle 3 with its base 7 on the cover 4. In the case of said exemplary embodiment, the receiving cradle 3 is to be inserted into the cover interior 19 of the cover 4. In this case, this can also be called a receiving position for the receiving cradle 3 in the cover 4. As a result of providing positioning elements 26, the receiving cradle 3, relatively with reference to the standing area (footprint) defined by the cover 4, is aligned in a so-called positioning position positioned for automated sample processing. This means that the standardized footprint is not defined or determined by the receiving cradle 3, but rather the cover 4 serves as an adapter element for the receiving cradle 3.

Consequently, the possibility is created to be able to realize the receiving cradle 3 pertaining to the respective requirements and dimensions independently of the standardized footprint. In this case, the standardized footprint for the pipette-tip-accommodating container 1 is realized for the receiving cradle 3 only in combination with the cover 4 as an adapter element.

The extent or the size of the standardized standing area (footprint) is determined, for example, by the American National Standards Institut (ANSI) in standard SLAS 1-2004 (R2012).

According to said standard for establishing or the size of the standardized standing area (footprint), the length dimension 23 comprises a value of 127.76 mm±0.25 mm. The width dimension 24, in turn, comprises a value of 85.48 mm±0.25 mm.

If the receiving cradle 3 is situated in the positioning position thereof, e.g. inside the cover 4, it can be supported directly on the cover wall 14. The base 7 of the receiving cradle 3 can consequently rest directly on the inside of the cover wall 14.

Side walls 8 to 11, which are arranged directly one behind another in the peripheral direction, form, in each case between them, transition regions 27 or corner regions. In the present exemplary embodiment, the transition regions 27 protrude outward in each case in the corner regions realized by the side walls 8 to 11. The receiving cradle 3 is supported on the positioning elements 26 at least in portions in each case in its transition regions 27 and in the peripheral region facing the base 7. In a preferred manner, two positioning elements 26 are provided in each case on or in the cover 4 for each of the transition regions 27 of the receiving cradle 3. As a result, each of the transition regions 27—that is to say the receiving cradle 3—can be positioned clearly between the side walls 8 to 11 in each of its corner regions. In a preferred manner, the positioning elements 26 are realized in a web-shaped or rib-shaped manner. The positioning elements 26 assigned in each case to a transition region 27 or corner region comprise an alignment at an angle of 90° with respect to one another.

If the receiving cradle 3 is situated in the positioning position thereof in the cover 4, side walls 8 to 11 of the receiving cradle 3 and cover side walls 15 to 18 of the cover 4, which are arranged in each case directly adjacent one another, are aligned extending substantially parallel to one another, when seen in the peripheral direction.

With the receiving cradle 3 in the positioning position, it is aligned centrally with reference to the footprint defined by the cover 4. Centrally is to be understood here in that in the positioning position, the center of the receiving cradle 3 is arranged congruent with reference to the center of the cover 4. Where the centering receiving means 6 is arranged and aligned correspondingly in the carrier 5, the pipette tips 2 are also consequently aligned and arranged in a clear relative position with reference to the defined footprint.

Furthermore, in the case of said exemplary embodiment, it is shown that the receiving cradle 3 is realized in a single-walled manner at least in the region of its side walls 8 to 11. A smaller material requirement can suffice as a result.

To support the carrier 5 in the region of the receiving opening 12 of the receiving cradle 3, part portions of the side walls 8 to 11 can be offset into the receiving area 13. As a result of said inward offsetting, a simpler realization of the receiving cradle 3 can thus be achieved using injection molding technology and nevertheless the inwardly projecting part portions of the side walls 8 to 11 realize a contact area or support for the carrier 5.

Furthermore, the side walls 8 to 11 of the receiving cradle 3, when viewed in axial section, can be realized tapering in a conical manner in each case proceeding from the receiving opening 12 in the direction toward the base 7. As a result, not only can removing the receiving cradle 3 from the mold be made easier, but also, by choosing and sizing the conical tapering in a corresponding manner, it is also possible to stack structurally identical receiving cradles 3 inside one another. To this end, a clear cross sectional dimension of the receiving cradle 3 is to be realized larger in the region of its receiving opening 12 than an outer cross sectional dimension of the receiving cradle 3 in the region of the base 7. As a result, it is possible for structurally identical receiving cradles 3 to be able to be stacked inside one another, as can be seen from the representation in FIG. 7.

In order to be able to determine a predefined stack measurement and consequently the extent of the nesting inside one another of the structurally identical receiving cradles 3, at least one first stacking means 28 can be arranged or realized on the receiving cradle 3 in the region of its receiving area 13. A further structurally identical receiving cradle 3 is supportable on said at least one first stacking means 28. In the present exemplary embodiment, the base 7 of the receiving cradle 3, for example, at least in regions, can realize a further stacking means 29.

As can now be seen better in FIG. 1, the cover 4, in its closed position, can be held locked on the receiving cradle 3 by means of at least one closing device 30. The at least one closing device 30 shown here can include a first closure element 31 on the cover 4 and a second closure element 32, which interacts with said first closure element, on the receiving cradle 3.

FIG. 1 shows the originally non-deformed position of the first closure element 31, the two closure elements 31, 32 being situated in a locked or closed position not yet engaged with one another. The present exemplary embodiment shows that the first closure element 31 is realized in a lobe-shaped manner and comprises a recess or breakthrough in the connecting region to the cover 4 for receiving the second closure element 32. Consequently, the first closure element 31 is able to engage behind the second closure element 32 with its recess. Furthermore, the at least one first closure element 31 is connected to the cover 4 so as to be pivotable.

Figure 6:
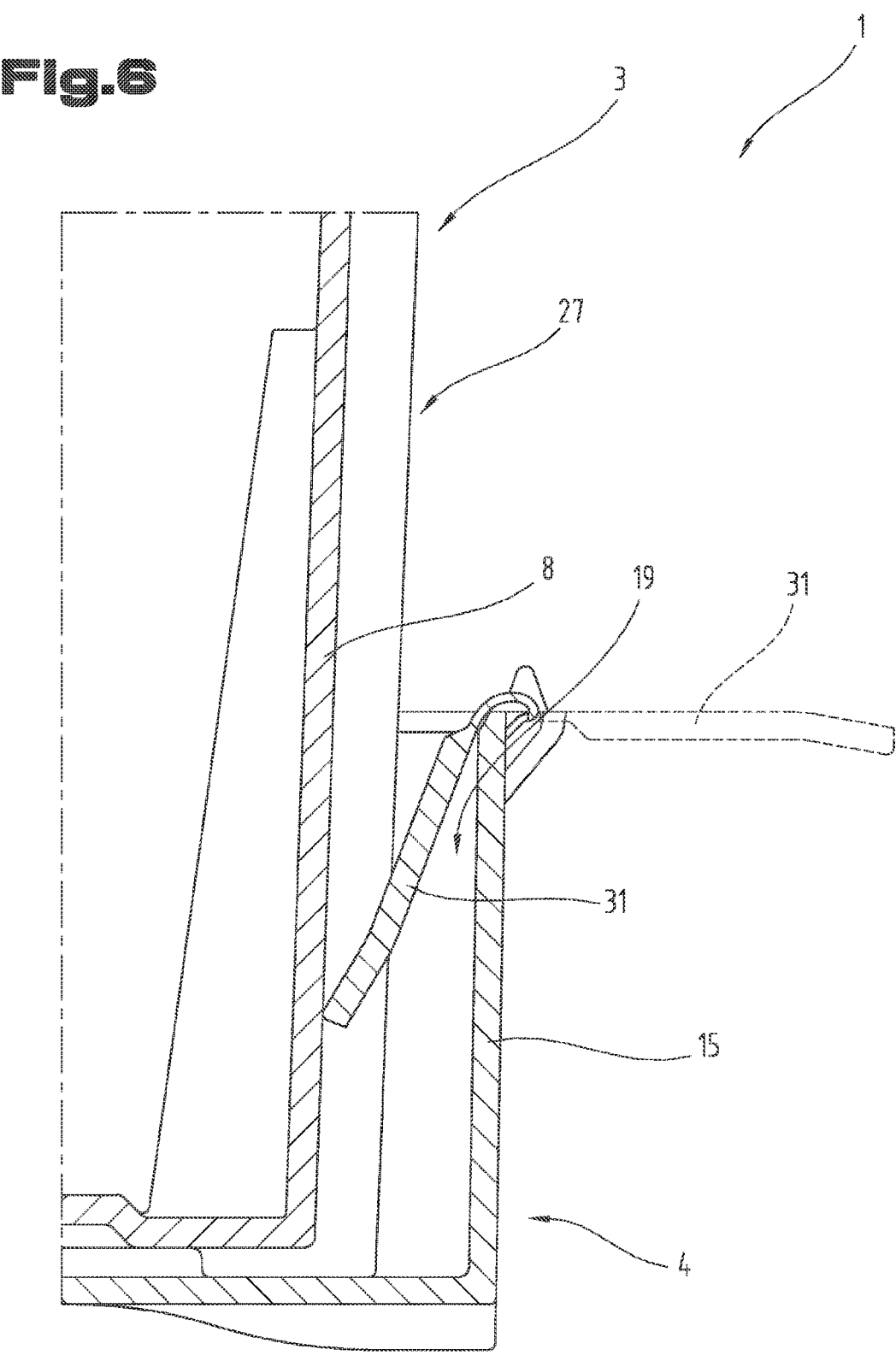
FIG. 6 shows a side view sectioned according to the lines VI-VI in FIG. 3 of another part detail of the cover and of the receiving cradle accommodated therein with a closure element supported on a side wall of the receiving cradle.
Figure 7:
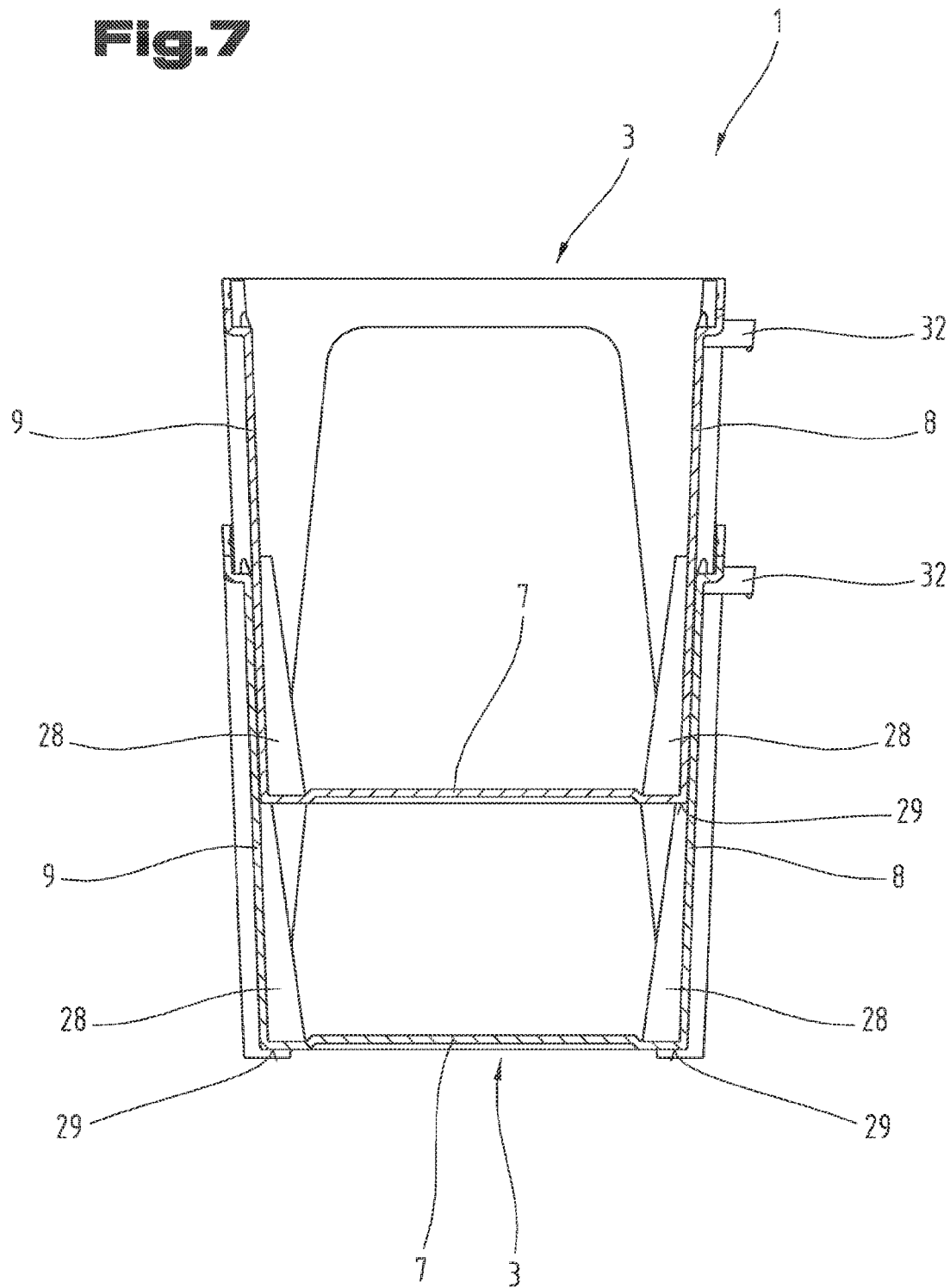
FIG. 7 shows a side view in section of a part detail of structurally identical receiving cradles, in a position stacked inside one another.

As a result, it is possible, as is shown in FIG. 6, with the receiving cradle 3 situated in the positioning position, for the first closure element 31 to be pivoted into the cover interior 19 and to project in the direction of the cover wall 14. In said position, the first closure element 31 then abuts against the side wall 8 to 11 of the receiving cradle 3 arranged in each case directly adjacent thereto. The non-deformed original position of the first closure element 31 is shown in dot dash lines, the deformed position being shown in solid lines.

As a result of said inward pivoting of the lobe-shaped first closure element 31, the receiving cradle 3, in the positioning position in the cover 4, can be acted upon additionally with an actuating force which is aligned approximately parallel with reference to the cover wall 14, and acts on the side wall 8 to 11 of the receiving cradle 3, facing said cover wall in each case. As a result of the built-up actuating force, the receiving cradle 3 is pressed in the effective direction of the same against at least individual positioning elements of the positioning elements 26 on the respectively oppositely situated side. As a result, an additional holding or fixing action can be obtained between the receiving cradle 3 and the cover 4 in the positioning position thereof.

The method for providing the pipette-tip-accommodating container 1, as described briefly below, can include the following steps. The individual pipette tips 2 are produced in the most varied sizes and in each case similar of the same are received positioned on the previously described carrier 5. Multiple carriers 5 are mostly put together with the respective pipette tips 2 to form a consumer stack and are provided in a consumer unit depending on quantity and size.

The pipette-tip-accommodating container 1 then serves for the purpose of receiving one of the carriers 5 in the region of its receiving opening 12 of the receiving cradle 3 and holding it there in a positioned manner Various possibilities are conceivable for providing the pipette-tip-accommodating containers 1. Thus, for example, only the receiving cradle 3 with the cover 4 held thereon, but without the carrier 5 received therein and consequently also without the pipette tips 2, could be supplied to the operator or user. He can then, depending on the requirement, remove a carrier 5 together with the pipette tips 2 held thereon out of one of the consumer units and insert it into the open receiving cradle 3.

However, it would also be possible for the pipette-tip-accommodating container 1 together with the carrier 5 received therein and with the pipette tips 2 held there to be supplied to the operator or user.

Depending on the application and use, individual or multiple of the pipette tips 2 can be removed either manually or in an automated removal operation by means of a pipettor (not shown) with the cover 4 open. Thus, in the case of said exemplary embodiment, the receiving cradle 3 serves in principle for the purpose of receiving the carrier 5 together with the pipette tips 2 arranged or received thereon positioned for removal. If the pipette tips 2 are completely removed from the carrier 5, the empty carrier 5 is removed from the receiving cradle 3 and a new carrier 5 provided with pipette tips 2 is able to be inserted, in turn, into the receiving opening 12 of the receiving cradle 3.

Consequently, the pipette-tip-accommodating container 1 in its basic form includes the receiving cradle 3 and the cover 4 which is held thereon so as to be removable. In a preferred manner, the receiving cradle 3 and the cover 4 are produced separately from one another and can be moved into a combined or joined position for delivery. The carrier 5 with the pipette tips 2 can be already have been received or is to be inserted in retro. In said so-called closed position of the cover 4, it covers the receiving opening 12 of the receiving cradle 3.

For manual handling or removal of the pipette tips 2, the cover 4 is to be opened by a certain amount or removed from the receiving cradle 3 such that unobstructed access to the individual pipette tips 2 is made possible.

For automated removal of pipette tips 2 or for sample processing, it is provided here that the cover 4 not only forms a closure element for the receiving cradle 3, but additionally also serves as an adapter element for the receiving cradle 3. To this end, as described previously, the positioning device 25 is provided with multiple positioning elements 26 which are arranged distributed, in a preferred manner over the periphery of the cover 4, in the cover interior 19 in the region of its cover wall 14 and/or on the side of the cover wall 14 turned away from the cover interior 19. Over and above this, the cover 4 is realized in its outer peripheral region at least in regions with the standardized footprint, the length dimension 23 and the width dimension 24 aligned at a right angle thereto being defined by the standardized footprint.

To form the adapter position of the cover 4 for the receiving cradle 3, the cover 4 is to be removed from the receiving cradle 3. The receiving cradle 3 is then supported with its base 7 on the cover 4. To this end, the receiving cradle 3 can either be inserted into the cover interior 19 of the cover 4 or can be placed on the cover wall 14 on the side turned away from the cover interior 19. By means of the previously described positioning elements 26, the receiving cradle 3 is then aligned thereto relatively with reference to the footprint defined by the cover 4 positioned in a precise positioning position. As a result, in the position positioned with respect to one another, the cover 4 realizes the adapter position for the receiving cradle 3 for automated sample processing or for removal of individual of the pipette tips 2. However, pipette tips 2 filled independently thereof could also be inserted into the carrier 5.

Figure 8:
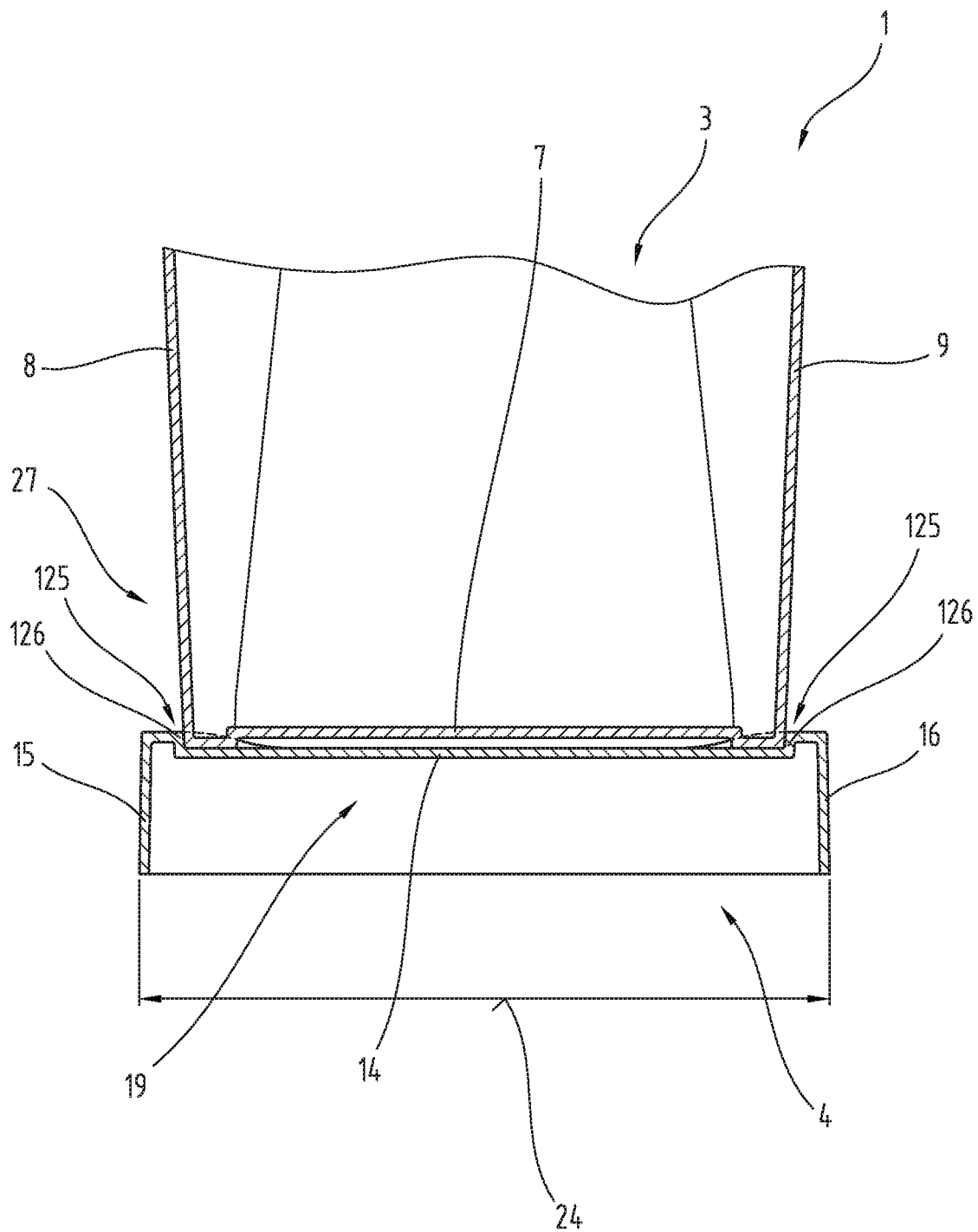
FIG. 8 shows a side view in section of a part detail of a further possible arrangement of the receiving cradle and of the cover as an adapter element.

FIG. 8 shows a further embodiment of the pipette-tip-accommodating container 1 which, where applicable, is independent in itself, identical reference signs or component designations being used, once again, for identical parts, as in preceding FIGS. 1 to 7. In order to avoid unnecessary repetition, the detailed description in the preceding FIGS. 1 to 7 is pointed out or referred to.

As said realization provides a possible alternative to the arrangement already described in more detail in FIG. 5, only the differences thereto will be described in more detail here.

The cover 4 is also realized here as an adapter element for the receiving cradle 3. The positioning device 125, in contrast to the previously described realization, is not arranged or realized in the region of the cover interior 19, but on the side of the cover wall 14 turned away from the cover interior 19. As a result, the open side of the cover 4—that is to say the cover side walls 15 to 18—serves as footprint in the positioned adapter position. As a result, the cover 4, at least in said portion, is to be realized in its dimensions with the standardized footprint, as has already been described previously.

The positioning elements 126 can be formed by corresponding realization of the cover wall 14 itself and/or by one or multiple webs or ribs. In the present exemplary embodiment, the positioning elements 126 could also serves at the same time as aligning or stacking aids for the forming of stacks of multiple pipette-tip-accommodating containers 1 stacked one above another. It was already known for forming a stack of multiple pipette-tip-accommodating containers 1 stacked one above another, for example, to allow the outer peripheral edge of the cover 4 to project somewhat beyond the cover wall 14, however, no precise positioning with respect to one another having been possible on account of the generous tolerances. In addition, the cover did not comprise the standardized footprint.

Furthermore, however, it would also be possible to realize or arrange both the positioning device 25 described beforehand in FIGS. 1 to 6 in the region of the cover interior 19 and the arrangement of the same described here in FIG. 8 on a cover 4 at the same time. An even more universal use of the cover 4 can be achieved as a result.

The exemplary embodiments show possible realization variants and application examples of the pipette-tip-accommodating container 1, it being noted at this point that the invention is not limited to the specially shown realization variants of the same, but rather diverse combinations of the individual realization variants amongst one another are also possible and said variation option is within the knowledge of the expert active in said technical field on account of the teaching for technical action as a result of objective invention.

The scope of protection is determined by the claims. The description and the drawings are to be used, however, for interpreting the claims. Individual features or feature combinations from the various exemplary embodiments shown and described can represent independent inventive solutions in themselves. The object underlying the independent inventive solutions can be found in the description.

All the specifications concerning value ranges in the description of the object are to be understood such that they include arbitrary and all part ranges, for example, the specification 1 to 10 is to be understood such that all part ranges, proceeding from the lower limit 1 and the upper limit 10 are included therein, i.e. all the part ranges begin with a lower limit of 1 or greater and end with an upper limit of 10 or less, for example 1 to 1.7, or 3.2 to 8.1, or 5.5 to 10.

As a matter of form, it must finally be pointed out that for better understanding of the design of the pipette-tip-accommodating container 1, the same or the component parts thereof have been shown in part not true to scale and/or enlarged and/or reduced.

LIST OF REFERENCES

1 Pipette-tip-accommodating container
2 Pipette tip
3 Receiving cradle
4 Cover
5 Carrier
6 Centering receiving means
7 Base
8 Side wall
9 Side wall
10 Side wall
11 Side wall
12 Receiving opening
13 Receiving area
14 Cover wall
15 Cover side wall
16 Cover side wall
17 Cover side wall
18 Cover side wall
19 Cover interior
20 Pivoting arrangement
21 Pivot pin
22 Pivot eyelet
23 Length dimension
24 Width dimension
25 Positioning device
26 Positioning element
27 Transition region
28 First stacking means
29 Further stacking means
30 Closing device
31 First closure element
32 Second closure element

The invention claimed is:

1. A pipette-tip-accommodating container (1) for accommodating a plurality of pipette tips (2), including
a receiving cradle (3) having a base (7) and side walls (8 to 11) which project up from the base (7), which side walls (8 to 11) surround a receiving opening (12) at least in regions and together with the base (7) define a receiving area (13);
a cover (4) having a cover wall (14) and having cover side walls (15 to 18) which stand out from the cover wall (14), which cover side walls (15 to 18) together with the cover wall (14) define a cover interior (19);
wherein the cover (4), in its closed position, covers the receiving opening (12) of the receiving cradle (3) and is held on the receiving cradle (3) so as to be removable;
wherein the cover (4), in its outer peripheral region at least in portions, defines a footprint with a length dimension (23) with a value of 127.76 mm±0.25 mm and with a width dimension (24), which is aligned at right angles thereto, with a value of 85.48 mm±0.25 mm;
wherein a positioning device (25) with multiple positioning elements (26) that are arranged over the outer peripheral region of the cover (4), is provided on the cover (4);
wherein the cover (4), in an open position removed from the receiving cradle (3), forms an adapter element for the receiving cradle (3);
wherein the receiving cradle (3), with the cover (4) in the removed open position, is supported by way of its base (7) on the cover (4), which has been removed from the receiving cradle (3), for forming an adapter position, and in said adapter position, the receiving cradle (3) is aligned relatively with reference to the footprint defined by the cover (4) positioned in a positioning position for automated sample processing by means of the positioning elements (26); and
wherein the side walls (8 to 11) of the receiving cradle (3) are realized tapering conically when seen in axial section in each case proceeding from the receiving opening (12) toward the direction of the base (7) and wherein the receiving cradle (3) comprises a clear cross sectional dimension in the region of its receiving opening (12) which is realized greater than an outer cross sectional dimension of the receiving cradle (3) in the region of the base (7).

2. The pipette-tip-accommodating container (1) as claimed in claim 1, wherein the positioning device (25) is arranged or realized in the cover interior (19) of the cover (4) and in the region of its cover wall (14).

3. The pipette-tip-accommodating container (1) as claimed in claim 1, wherein the positioning device (25) is arranged or realized on a side of the cover wall (14) facing away from the cover interior (19).

4. The pipette-tip-accommodating container (1) as claimed in claim 1, wherein the receiving cradle (3) is supported directly on the cover wall (14) in the positioning position thereof.

5. The pipette-tip-accommodating container (1) as claimed in claim 1, wherein the receiving cradle (3) is supported in each case in transition regions (27) between the side walls (8 to 11), which are arranged one behind another in the peripheral direction, against said side walls and in the peripheral region thereof facing the base (7) against said positioning elements (26).

6. The pipette-tip-accommodating container (1) as claimed in claim 5, wherein two positioning elements (26) are provided on the cover (4), in particular on the cover wall thereof (14), for each of the transition regions (27) of the receiving cradle (3).

7. The pipette-tip-accommodating container (1) as claimed in claim 1, wherein with the receiving cradle (3) situated in the positioning position, it is aligned centrally with reference to the footprint defined by the cover (4).

8. The pipette-tip-accommodating container (1) as claimed in claim 1, wherein the cover (4) is pivotably mounted on the receiving cradle (3) by means of at least one pivoting arrangement (20).

9. The pipette-tip-accommodating container (1) as claimed in claim 1, wherein the receiving cradle (3) is realized in a single-walled manner in the region of its side walls (8 to 11).

10. The pipette-tip-accommodating container (1) as claimed in claim 1, wherein at least one first stacker (28) is arranged or realized on the receiving cradle (3) in the region of its receiving area (13), and a further structurally identical receiving cradle (3) is insertable into the receiving area (13) and is supportable on the at least one first stacker (28).

11. The pipette-tip-accommodating container (1) as claimed in claim 10, wherein the base (7) of the receiving cradle (3) at least in regions forms a second stacker (29).

12. The pipette-tip-accommodating container (1) as claimed in claim 1, wherein a carrier (5) with centering receiving means (6) arranged therein for the aligned receiving of the pipette tips (2) is arranged or realized in the receiving cradle (3) in the region of its receiving opening (12).

13. The pipette-tip-accommodating container (1) as claimed in claim 1, wherein, in its closed position, the cover (4) is held in a locked manner on the receiving cradle (3) by means of at least one closing device (30), wherein the at least one closing device (30) includes a first closure element (31) on the cover (4) and a second closure element (32) which interacts therewith on the receiving cradle (3).

14. The pipette-tip-accommodating container (1) as claimed in claim 13, wherein the first closure element (31), which is arranged on the cover (4), in particular on at least one of its cover side walls (15 to 18), is realized in a lobe-shaped manner and is connected to the cover (4) so as to be pivotable, and wherein, with the receiving cradle (3) situated in the positioning position, the first closure element (31) is pivoted into the cover interior (19) and abuts against the side wall (8 to 11) of the receiving cradle (3) which is arranged directly adjacent.

15. A method for providing a pipette-tip-accommodating container (1) for receiving a plurality of pipette tips (2), the method comprising:
- forming a receiving cradle (3) with a base (7) and with side walls (8 to 11) which project up from the base (7), wherein the side walls (8 to 11) surround a receiving opening (12) at least in regions and define a receiving area (13) together with the base (7);
- wherein the side walls (8 to 11) of the receiving cradle (3) are realized tapering conically when seen in axial section in each case proceeding from the receiving opening (12) toward the direction of the base (7) and wherein the receiving cradle (3) comprises a clear cross sectional dimension in the region of its receiving opening (12) which is realized greater than an outer cross sectional dimension of the receiving cradle (3) in the region of the base (7);
- forming a cover (4) with a cover wall (14) and with cover side walls (15 to 18) which stand out from the cover wall (14), wherein the cover side walls (15 to 18) together with the cover wall (14) define a cover interior (19); and
- with the cover (4) in a closed position, covering the receiving opening (12) of the receiving cradle (3) and holding the cover (4) removably on the receiving cradle (3) wherein the cover (4) is movable into an open position after removal from the receiving cradle (3);
- wherein the cover (4), in its outer peripheral region at least in portions, is realized with a length dimension (23) with a value of 127.76 mm±0.25 mm and a width dimension (24), which is aligned at right angles thereto, with a value of 85.48 mm±0.25 mm;
- providing on the cover a positioning device (25) with multiple positioning elements (26) that are arranged over the outer peripheral region of the cover (4);
- removing the cover (4) from the receiving cradle (3) and moving the cover into an open position of the cover and then supporting the receiving cradle (3) on the cover (4) by way of the base (7) to form by the cover an adapter element for forming an adapter position for the receiving cradle (3);
- wherein the receiving cradle (3) is aligned relatively with reference to the footprint defined by the cover (4) positioned in the adapter position by moans of the positioning elements (26); and
- wherein in the adapter position, the cover (4) realizes a positioning position for the receiving cradle (3) for automated sample processing in the position positioned with respect to one another.

16. The method as claimed in claim 15, wherein the receiving cradle (3), in the positioning position thereof on the cover (4), is aligned centrally with reference to the footprint defined by the cover (4).

17. The method as claimed in claim 15, wherein the receiving cradle (3), in the positioning position thereof in the cover (4), is acted upon additionally with an actuating force, which is aligned approximately parallel with reference to the cover wall (14), acting on at least one of its side walls (8 to 11) and the receiving cradle (3) is pressed in the effective direction of the actuating force by said force against at least individual positioning elements of the positioning elements (26).

* * * * *